United States Patent
Melman et al.

(10) Patent No.: US 8,078,244 B2
(45) Date of Patent: Dec. 13, 2011

(54) INTERFEROMETRIC METHOD AND INSTRUMENT FOR MEASUREMENT AND MONITORING BLOOD GLUCOSE THROUGH MEASUREMENT OF TISSUE REFRACTIVE INDEX

(75) Inventors: Paul Melman, Newton, MA (US); Stephen Cohen, Chestnut Hill, MA (US)

(73) Assignee: Newton Photonics, Inc., Chesnut Hill, MA (US)

( * ) Notice: Subject to any disclaimer, the term of this patent is extended or adjusted under 35 U.S.C. 154(b) by 1399 days.

(21) Appl. No.: 11/610,268

(22) Filed: Dec. 13, 2006

(65) Prior Publication Data

US 2007/0135693 A1 Jun. 14, 2007

Related U.S. Application Data

(60) Provisional application No. 60/750,271, filed on Dec. 14, 2005.

(51) Int. Cl.
*A61B 5/1455* (2006.01)
(52) U.S. Cl. .................... 600/316; 600/310
(58) Field of Classification Search .............. 600/316, 600/322, 365, 310, 473
See application file for complete search history.

(56) References Cited

U.S. PATENT DOCUMENTS

| 6,485,703 | B1 | 11/2001 | Cote et al. | |
|---|---|---|---|---|
| 6,725,073 | B1 | 4/2004 | Motamedi et al. | |
| 2003/0023151 | A1 | 1/2003 | Khalil et al. | |
| 2005/0171438 | A1* | 8/2005 | Chen et al. | 600/476 |
| 2006/0063988 | A1* | 3/2006 | Schurman et al. | 600/316 |
| 2006/0264719 | A1 | 11/2006 | Schurman et al. | |

OTHER PUBLICATIONS

Larin et al. "Specificity of noninvasive blood glucose sensing using optical coherence tomography technique: a pilot study", Phys. Med. Biol. 48 (2003) pp. 1371-1390.*
International Search Report dated Jun. 5, 2009.
Written Opinion dated Jun. 5, 2009.

* cited by examiner

*Primary Examiner* — Eric Winakur
*Assistant Examiner* — Chu Chuan (JJ) Liu
(74) *Attorney, Agent, or Firm* — Nields, Lemack & Frame, LLC

(57) ABSTRACT

A method of measuring glucose concentration in tissue includes measuring scattering coefficients of the tissue at each of a plurality of temperatures and at a selected tissue depth using optical coherence tomography, and determining the glucose concentration in interstitial fluid of the tissue as a function of the measured scattering coefficients.

22 Claims, 4 Drawing Sheets

FIGURE 1

INTERFEROMETRIC METHOD AND INSTRUMENT FOR MEASUREMENT AND MONITORING BLOOD GLUCOSE THROUGH MEASUREMENT OF TISSUE REFRACTIVE INDEX

This application claims the benefit of U.S. Provisional Application No. 60/750,271 filed Dec. 14, 2005, which is incorporated by reference herein in its entirety.

BACKGROUND

Diabetes mellitus is a prevalent disease that costs the American public over $5 billion/year in invasive testing procedures and $132 billion/year in related healthcare costs. Types I and II diabetes affect an estimated 171 million people in the world today. The disease is generally manifested by disorders in blood levels of insulin, a pancreatic hormone that helps convert glucose into energy. Insulin is necessary for glucose absorption by cells. Unused glucose remains in the blood and is then removed by the kidneys.

Type 1 diabetes, sometimes called insulin-dependent diabetes or juvenile-onset diabetes, results from a shortage of insulin. With Type 1 diabetes the pancreas makes little or no insulin usually because insulin-producing beta cells have been destroyed. Type 1 diabetes usually appears suddenly and most commonly in those under age 30. Type 2 diabetes, also known as noninsulin-dependent diabetes or adult-onset diabetes, usually results from the body's inability to process insulin effectively. With Type 2 diabetes, the pancreas generally makes some insulin. However, the insulin is not effective because of the cell membrane resistance to penetration. About 90 to 95 percent of all people with diabetes have Type 2 diabetes.

Diabetes sufferers must monitor their blood glucose levels regularly to avoid long term complications from hyperglycemia (an overabundance of blood glucose) as well as symptoms of hypoglycemia (a deficiency of blood glucose). Long-term complications from hyperglycemia can damage the eyes, nervous system, kidneys, and cardiovascular and circulatory systems, as well as hinder the body's overall resistance to infections. Cuts and sores may heal more slowly and diabetics are prone to gum problems, urinary tract infections, and mouth infections. Symptoms of hypoglycemia include weakness, dizziness, disorientation, tingling in the hands and feet, and rapid heartbeat.

The proper treatment of diabetes includes maintenance of blood glucose at normal levels, thus frequent monitoring of blood glucose concentration is extremely important in maintaining health and reducing risks from complications. Blood glucose monitoring at this time is generally accomplished by obtaining a droplet of blood for further analysis, usually by a finger prick. This is inconvenient and invasive, usually resulting in infrequent testing. Non-invasive blood glucose monitoring has a high medical and economic value and has attracted an intense interest in the scientific, medical and financial communities. Non-invasive monitoring could dramatically improve disease management and quality of life of stricken individuals through more frequent testing and timely detection of changes in blood glucose level.

Most non-invasive techniques utilize some type of spectral analysis. However, one of the major obstacles in glucose measurement by spectral methods is the interference of the tissue matrix. The water containing tissue in which the glucose measurement needs to be performed has the highest transparency in the wavelength range of 0.8-1 µm. However this is also the range where the glucose spectral signature is relatively weak and thus hard to separate from the matrix. In contrast, in the spectral region where glucose has well defined spectral features (mid-IR) the tissue water absorption is high and therefore the optical path is very short. This coincidence of spectral features makes non-invasive blood glucose monitoring by spectral absorption or emission especially challenging.

SUMMARY

The disclosed embodiments include a method of measuring glucose concentration in tissue. The method includes measuring scattering coefficients of the tissue at each of a plurality of temperatures and at a selected tissue depth using optical coherence tomography, and determining the glucose concentration in interstitial fluid of the tissue as a function of the measured scattering coefficients.

The disclosed embodiments also include a system for measuring glucose concentration in tissue. The system includes a probe for applying a plurality of temperatures to the tissue, and an instrument for measuring a scattering coefficient of light scattered by the tissue at each of the plurality of temperatures at a selected tissue depth using an optical coherence tomography system, and for determining the glucose concentration in interstitial fluid of the tissue as a function of the measured scattering coefficients.

BRIEF DESCRIPTION OF THE DRAWINGS

The foregoing aspects and other features of the presently disclosed embodiments are explained in the following description, taken in connection with the accompanying drawings, wherein:

FIG. 1 shows a plot of a relative change in the scattering coefficient of tissue resulting from a change in glucose concentration in interstitial fluid;

DETAILED DESCRIPTION

Figure 2:
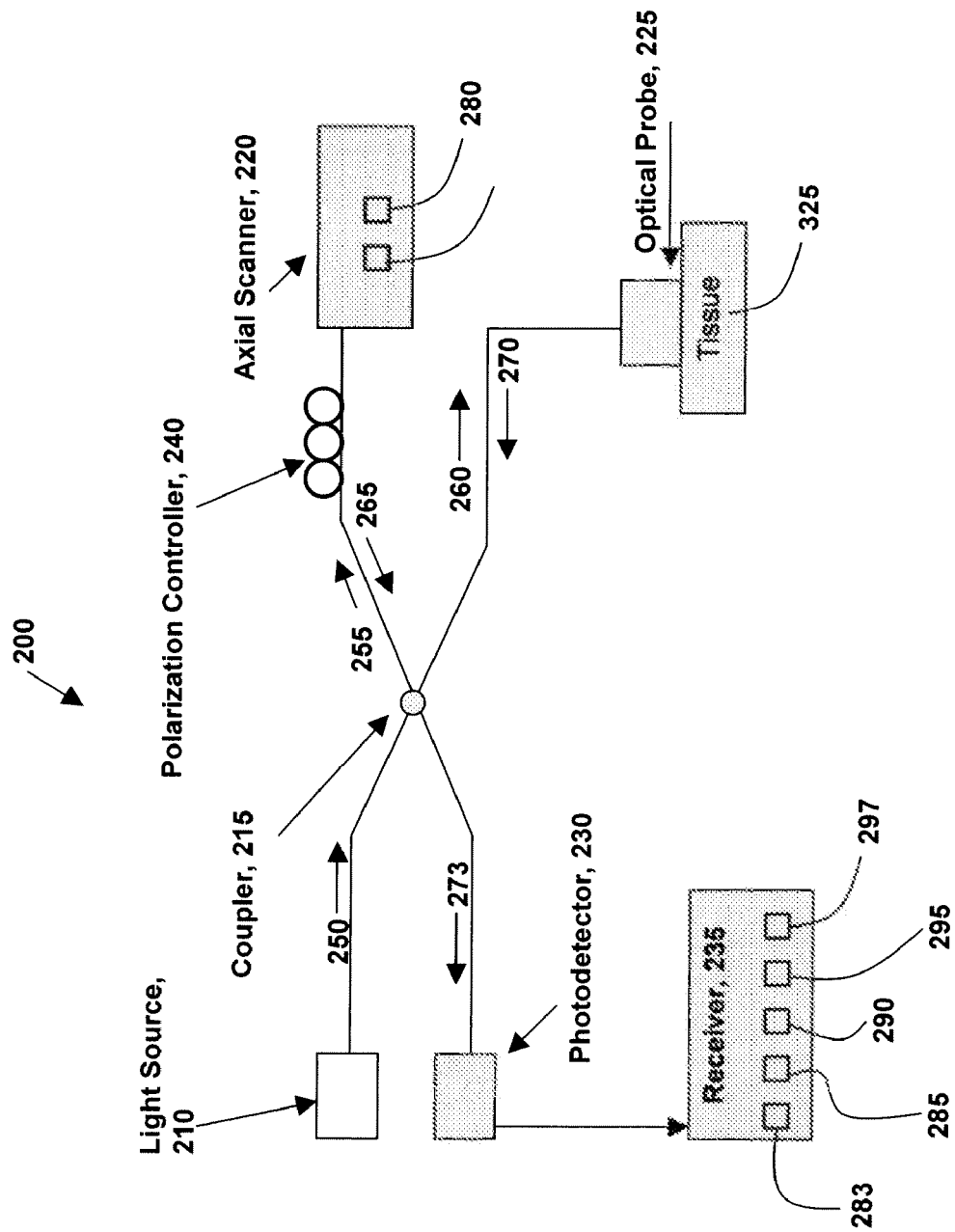
FIG. 2 shows a block diagram of a system suitable for practicing the disclosed embodiments.

Although the presently disclosed embodiments will be described with reference to the drawings, it should be understood that they may be embodied in many alternate forms. It should also be understood that in addition, any suitable size, shape or type of elements or materials could be used.

The disclosed embodiments include a structure and methodology for non-invasive blood glucose monitoring using a low coherence interferometer which overcomes the deficiencies of previous techniques. The disclosed embodiments advantageously exhibit high sensitivity, specificity and accuracy required for a practical portable blood glucose monitor.

The disclosed embodiments include at least a method and an instrument as an implementation of a noninvasive in-vivo monitor of blood glucose based on measurements of back-scattered light from tissue. Previous works use the scattering coefficient as a direct measure of glucose concentration in interstitial fluid. In contrast, it is a feature of the present embodiments to utilize a function of scattering coefficients, measured at a number of different temperatures, to extract the glucose concentration. An exemplary embodiment employs thermally modulated optical coherence tomography for this purpose.

The disclosed approach, in contrast to previous implementations, is independent of tissue parameters and thus independent of changing physiological effects. The scattering coefficient (amount of scattering as a function of propagation distance) generally depends on the glucose concentration in the interstitial fluid. Glucose concentration in interstitial fluid closely tracks the value of glucose concentration in blood and therefore is a valid measure of blood glucose. The main inaccuracy of previous scattering based methods stems from the dependence of the scattering coefficient on parameters other than tissue glucose. In general, light scattering properties of live tissue vary in time due to physiological processes, hydration levels, physical activities, emotional stress etc. These factors affect the scattering coefficient and thus interfere with glucose measurement.

The present embodiments include a method and system for blood glucose determination based on the dependence of scattering on tissue indices of refraction and therefore are less susceptible to interference caused by changes in tissue condition.

More specifically, the present embodiments take advantage of the sensitivity that optical coherence tomography achieves through its ability to interrogate a specific, selectable tissue layer beneath the skin, and an innovative use of thermal modulation to eliminate tissue-dependent interference from blood glucose determination. Data obtained using the described techniques and instrumentation may then be filtered to further improve measurement accuracy by minimizing optical distortions.

Light scattering is generally a function of 1) the source wavelength and 2) a scattering particle's size, concentration, and index difference with respect to the surrounding medium. For a complex medium such as tissue the total scattering intensity is a sum of the contributions from all particles present.

The disclosed embodiments are based on the innovative realization that the sensitivity of the scattering coefficient to changes in refractive index of the liquid ($n_l$) is significant only when the index difference between the scattering particles and the surrounding liquid is small. This holds true for both Mie and Rayleigh-Gans scattering regimes. Therefore, tissue can be viewed as being composed of scattering particles falling into one of two categories: those with index of refraction close to that of interstitial fluid (the so called "active" group), and those with index of refraction farther away from that of interstitial fluid (the so called "inactive" group).

Figure 1:
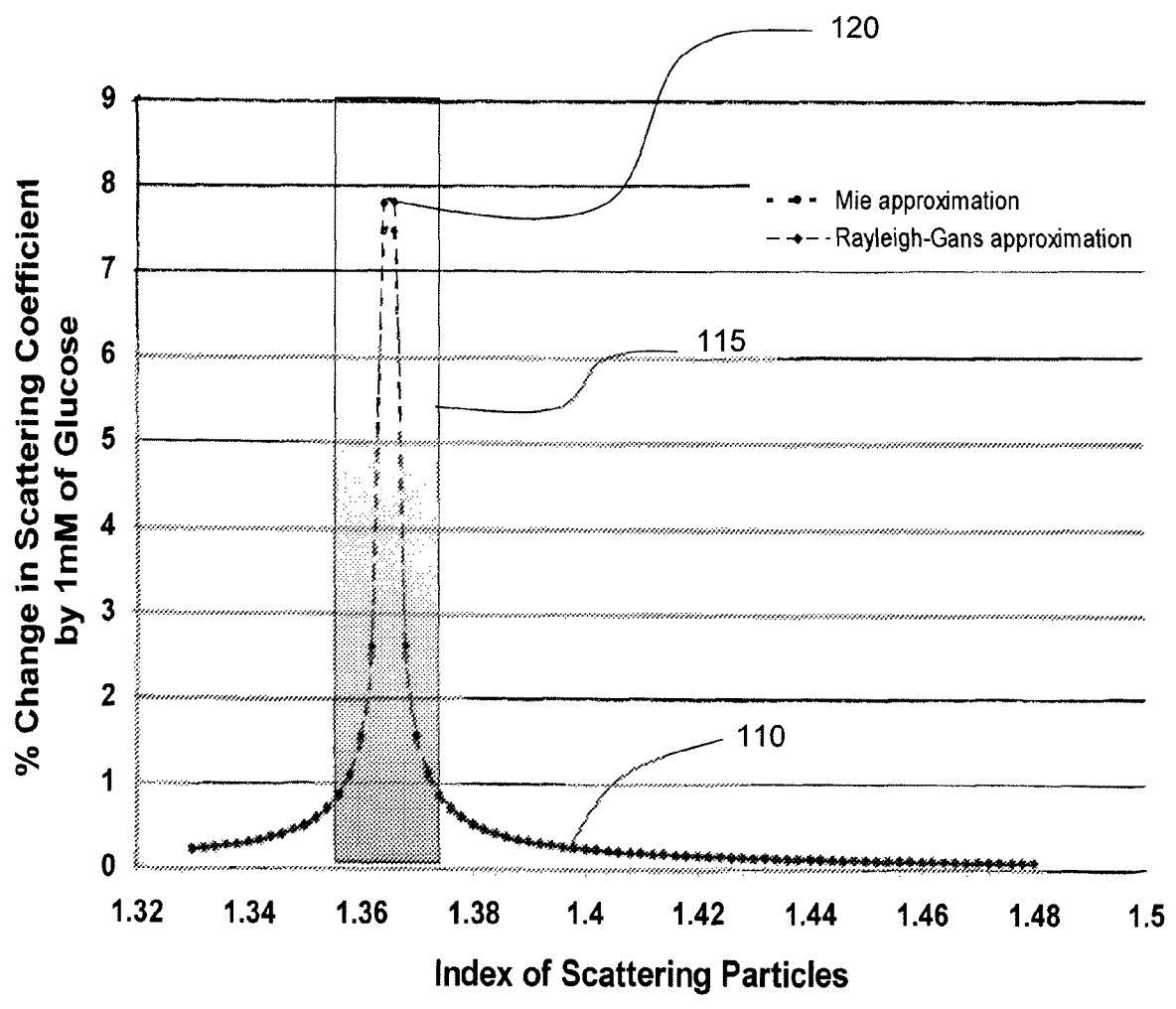

FIG. 1 shows a plot of this relative change in $\mu_s'$ (reduced scattering coefficient) 110 for 1 mM change in glucose concentration in interstitial fluid (with a nominal index of 1.365). FIG. 1 illustrates that components within a narrow range of index, that is, within shadowed area 115, for example, approximately +/−0.01 around the center of the peak response 120, affect the magnitude of scattering caused by changes in glucose concentration and hence make up the "active" group. The "inactive" group outside the shadowed area contributes a practically constant scattering background independent of glucose concentration.

The disclosed embodiments are also based on an additional innovative realization that the separation in measuring the contributions of "active" and "inactive" scatterers can be accomplished using temperature modulation. The temperature dependence of the scattering coefficient is due to the thermo-optic effect. The magnitude of this effect is an increase of 1° C. in water results in a reduction of the index of refraction ($\Delta n_T$) by $10^{-4}$. A change of tissue temperature in a short time period, for example, much less than the time it takes for physiological effects to occur (e.g. a few seconds), modifies only the optical properties of tissue.

Innovative use of temperature modulation is effective because it may be used to separate the "inactive" from the "active" part of the scattering coefficient. The contribution of "inactive" components" does not change with glucose concentration or temperature because it is outside the high response region 115 shown in FIG. 1. In contrast, scattering by the "active" components strongly depends on temperature and the absolute amount of change varies with glucose concentration. Furthermore this measurement depends only on the difference between the two temperatures and not on the starting (i.e. ambient temperature. Therefore, by measuring the scattering coefficient at two temperatures and subtracting the two values one can eliminate the contribution of the "inactive" scatterers.

Yet another innovative realization is that measurement at a third temperature allows the calculation of a second expression consisting of a constant geometrical term multiplying the differential of the optical terms for the 'active' scatterers only. The ratio of the two expressions eliminates the constant geometrical term and leaves a function of index of refraction that depends on glucose concentration only.

The disclosed embodiments may utilize optical coherence tomography for scattering measurement. Optical coherence tomography generally measures interference between a reference beam and a beam of light back-scattered from a sample under test. The interference signal generally occurs only when the path-length difference between the beams is near zero. This path-length may be varied in time by a moving mirror to generate depth scans of the sample. Unlike other scattering techniques, optical coherence tomography has the ability to measure light scattered at a selectable tissue depth. The tissue depth may extend to or exceed 2 mm and the depth may be selectable in microns. This capability allows for measuring a spatially resolved scattering coefficient and for tissue layer selection.

As a result of the innovative realizations in the context of optical coherence tomography and tissue temperature modulation, the following methodology may be derived for determining glucose concentration in interstitial fluid.

The scattering coefficient of tissue may be written as:

$$m_s' = f_b(a,d,\lambda) + f_s(a, d,\lambda)*f_m(c_g,T) \qquad 1.$$

where $m_s'$ is the reduced scattering coefficient (reduced here means modified to account for scattering anisotropy); $f_b(a,\rho,\lambda)$ is a background scattering coefficient (independent of glucose concentration and temperature); $f_s(a,d,\lambda)$ is a function of the physical parameters of the tissue; and $f_m(c_g,T)$ is a function of refractive indices of tissue components only. Here a is the average size of scattering particles; d their population density; $\lambda$ the wavelength of light; $c_g$ the glucose concentration; and T is the scattering tissue temperature. This form explicitly separates the contributions of the glucose independent scattering ("inactive components") from the glucose dependent part ("active components"). The functions $f_b(a,d,\lambda)$, $f_s(a,d,\lambda)$, $f_m(c_g,T)$ can be derived from scattering theories (e.g. Mie theory). Thus, equation 1 provides the basis for tissue independent glucose measurement.

Next, the scattering coefficient may be measured at three distinct temperatures. In order to measure glucose concentration without interference from tissue variations the function $f_m(c_g,T)$ may be extracted. This may be done by computing the following expression.

$$G_c = (m_s'(T1) - m_s'(T2))/(m_s'(T2) - m_s'(T3)) = (f1-f2)/(f2-f3) \qquad 2.$$

where f1, f2, and f3 are the values of the function $f_m(c_g,T)$ at three temperatures (T1, T2, T3). The glucose function $G_c$ is constructed from the three measured numbers and is independent of the physical tissue parameters. For a given tissue it is a function of glucose concentration only. Therefore, measurement of the tissue's scattering coefficient ($m_s'$) at three different temperatures provides a highly specific way of measuring glucose concentration without the interference of tissue parameters.

For tissue where the background coefficient $f_b(a,\rho,\lambda)$ is small compared to $f_s(a,\rho,\lambda)$ a two temperature method (T1, T2) can be used. In this case the tissue independent glucose function $G_c$ can be written as $$G_c = m_s'(T1)/m_s'(T2) \qquad 3.$$

The methodology may then involve computing a glucose concentration from the function $G_c$. This may be performed by either a simple calibration where the value of $G_c$ is compared to a blood reading or by using a scattering theory to express the explicit functional dependence of $G_c$ on glucose concentration. For example, using Mie theory the function $f_m(c_g,T)$ can be written as:

$$f_m(c_g,T) = ((n_s/n_m)-1)^{2.09} \qquad 4.$$

where $n_s$ is the index of refraction of scattering components of the tissue (e.g. solid cell components); and $n_m = n_{ISF} - T \times 10^{-4} + 2.73 \times 10^{-5} \times c_g$. Here $c_g$ is in units of mM and T is in degrees C. If $n_s$ and $n_{ISF}$ are known the measurement may be self calibrating in the sense that it directly yields glucose concentration.

FIG. 2 shows a block diagram of an exemplary system 200 suitable for practicing the embodiments disclosed herein. System 200 may include a light source 210, an optical coupler 215, an axial scanner 220, an optical probe 225, a photodetector 230, and a receiver 235. System 200 may also include a polarization controller 240. In one embodiment, the system components may be coupled together as an optical coherence tomography instrument, that is, an equal arm interferometer with the light source and axial scanner in the reference arm.

Light source 210 may be a broadband light source, emitting light in the near infrared range. Light source 210 may be implemented using a laser or an SLED. In one embodiment, light source 210 may be a broadband SLED with a spectral width of approximately 40-100 nm. The output 250 of light source 210 may be split into two equal intensity beams 255, 260 by optical coupler 215. A reference beam 265 may be reflected by axial scanner 220 while beam 260 may be coupled to optical probe 225 for illuminating sample tissue. Axial scanner 220 may include a scanning mirror, a fiber squeezer, a grating followed by a detector array, or any other device which provides axial resolution. Axial scanner may also include drive electronics 275 and a function generator 280. Optical probe 225 may illuminate sample tissue 325, apply one or more temperature differentials to the tissue and collect light scattered by the sample tissue. Optical probe 225 and its operation will be described in detail below. The scattered beam 270 may be combined with reference beam 265 by optical coupler 215 and coupled to photodetector 230. Photodetector 230 may be a standard PIN photodiode or a photodiode array.

The beat between scattered beam 270 and reference beam 265 is measured by photodetector 230. Photodetector 230 may convert the combined light beam 273 to an electrical signal for processing by the receiver 235. The receiver 235 may include a photodetector amplifier 283, data acquisition 285, signal processing 290, analysis 295, and control 297 functions implemented in hardware, software or a combination of hardware and software. The control functions 297 may include functions for controlling and coordinating the operations of the system components including light source 210, axial scanner 220, optical probe 225, photodetector 230, and polarization controller 240. Generally, the control functions 297 may include functions for controlling and coordinating the operations of the system components including light source 210, axial scanner 220, optical probe 225, photodetector 230, and polarization controller 240 to implement the methodology and embodiments described herein. The receiver 235 may have various connections (not shown) including power, control, and data connections to the system components for implementing the control and coordination functions.

Figure 3:
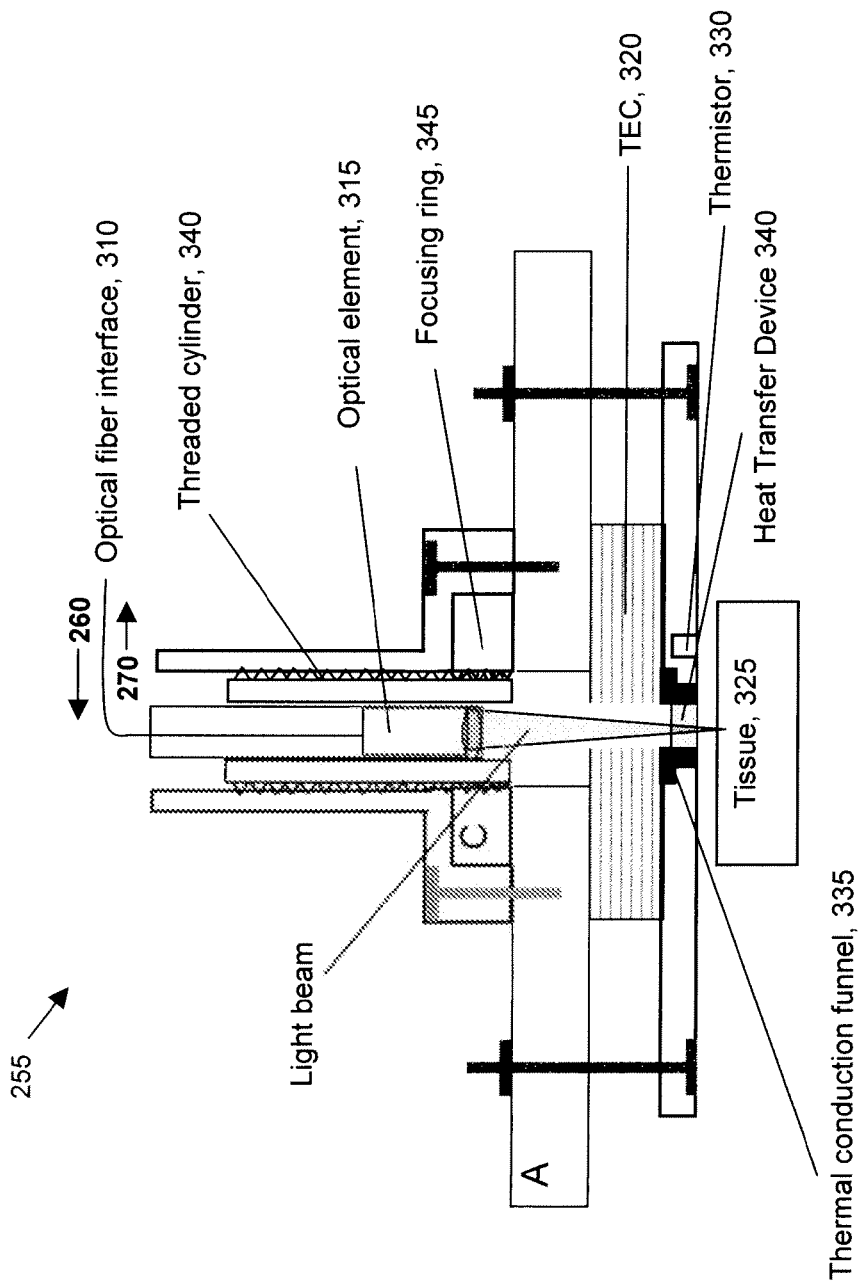
FIG. 3 shows a schematic diagram of an optical probe suitable for practicing the disclosed embodiments.

FIG. 3 shows a schematic diagram of optical probe 225. Optical probe 225 may include an optical fiber interface 310, an optical element 315, and a thermo-electric cooler/heater 320. Optical fiber interface 310 receives beam 260 from optical coupler 215 (FIG. 2) and conveys the beam to optical element 315 for illuminating sample tissue 325. Optical element 315 may be a lens or other focusing device. Optical element 315 may also be capable of translating beam 260 across the surface of sample tissue for obtaining a plurality of sample readings. Scattered light from sample tissue 325 is conveyed back through optical element 315 and through optical fiber interface 310 to optical coupler 215 as beam 270.

Thermo-electric cooler/heater 320 applies a temperature differential to sample tissue 325 in conjunction with the illumination under the control of control functions 297 in receiver 235 (FIG. 2). Thermo-electric cooler/heater 320 may be activated by current flow. For example, when current flows in one direction through thermoelectric cooler/heater 320 a first side may become hot while a second side becomes cold. Reversing the current flow may cause the first side to become cold and the second side to become hot. In one embodiment thermo-electric cooler/heater 320 may be a Peltier device. A thermistor 330 or other temperature measurement device may provide temperature feedback used to control thermo-electric cooler/heater 320.

Optical probe 225 may also have a thermal conduction funnel 335 for conveying thermal energy between thermoelectric cooler/heater 320 and sample tissue 325. A heat transfer device 340 may also be used to uniformly convey thermal energy between thermoelectric cooler/heater 320 and sample tissue 325 and across the surface of sample tissue 325. The heat transfer device 340 may be located within thermal conduction funnel 335. It must be optically clear at the light wavelengths employed by system 200. In one embodiment, the heat transfer device may be constructed of an optically transparent, thermally-conductive material. A threaded cylinder 340 and a focusing ring with mating threads may be used to position optical element 315 for focusing beams 260, 270.

System 200 may be self contained in a wearable device, having a form factor, for example, of a wristwatch. In other embodiments, some components, for example, receiver 235, may be separate from other components of the system and may communicate with the other components using a wired or wireless communication technique such as Bluetooth, IEEE 811, or any other appropriate communication method.

System 200 operates by energizing light source 210 and splitting its output between the reference arm ending with axial scanner 220 and the sample arm ending with optical probe 225 as described above. Temperature differentials are applied to sample tissue 325. The resulting scattered light differentials corresponding to the applied temperature differentials are conveyed to photodetector 230, converted to electrical signals and processed by receiver 235. The measured scattering coefficients at the different temperatures are separated into inactive components that do not change with glucose concentration and temperature and active components that do change with glucose concentration and temperature as described above. The active components are then used to determine the glucose concentration. The signal processing function 290 may be used for separating the scattering coefficients into their various components and computing the glucose concentration.

Figure 4:
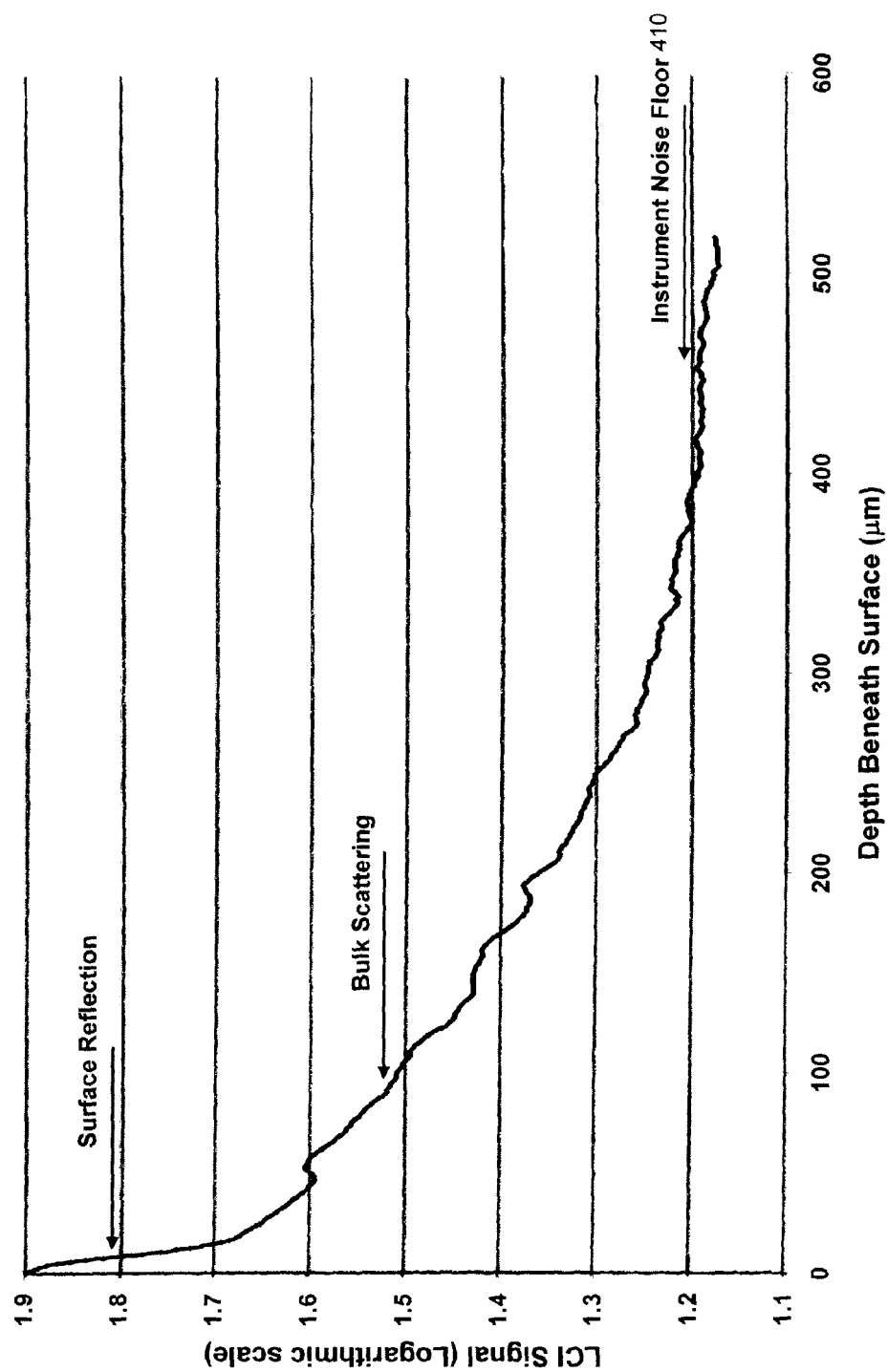
FIG. 4 shows an exemplary output of a photodetector of the system in FIG. 2.

FIG. 4 shows an exemplary output of photodetector amplifier 283 (FIG. 2). The output of photodetector amplifier 283 may be a logarithmic function of the input signal resulting from beam 273 (FIG. 2). Light scattering reduces the intensity of light propagating forward in the tissue in an exponential manner. Therefore a logarithmic amplifier output ideally generates a signal which may be a straight line having a negative slope. Actual output may not be a straight line due to noise and by optical distortions. FIG. 4 is an example of data acquired by system 200 of scattering in a tissue phantom (polystyrene spheres in glucose solution).

The effect of varying intensity resulting from the use of a focused beam is well described in the literature. For example, when using a Gaussian beam the light intensity varies along the propagation axis z according to the relationship $f(z)=(1+(w(z)/w(0))^2)$ where $w(z)$ is the Gaussian spot-size at distance z from the focal plane. To obtain the undistorted scattering coefficient the logarithmic signal may be corrected by subtracting $\log(f(z))/2$. Signal processing function 290 may be utilized to make these corrections.

The distorting phenomena that should be removed from the raw data include the following as described in paragraphs [042]-[046] below.

The effect of varying intensity resulting from the use of a focused beam is well described in the literature. For example, when using a Gaussian beam the light intensity varies as $f(z)=(1+(w(z)/w(0))^2)$ where $w(z)$ is the Gaussian spot-size at distance z from the focal plane. To obtain the undistorted scattering coefficient the logarithmic signal may be corrected by subtracting $\log(f(z))/2$. Signal processing function 290 may be utilized to make these corrections.

Polarization of light plays an important role in the quality of the signal received. A maximum signal is received when the light in both arms of the interferometer has the same polarization. Light source 210 may only be slightly polarized. However the reflected beam 270 may also have different polarization than the reference beam 265 due to scattering caused by birefringence of sample tissue 325. The interference is an instantaneous vector-addition of the two fields making the polarization effects present even in the case of unpolarized light. Human tissue exhibits various degrees of birefringence. When placed in the sample arm of the interferometer, more specifically when illuminated by optical probe 225, a birefringent matter creates a signal which is modulated with a period that depends on the degree of birefringence and an amplitude that depends on the light source's degree of polarization. In the case of completely unpolarized light, the maximum variation in the amplitude can be as large as a few dB. This level of modulation produces significant signal modulation affecting the slope measurement. One method of correcting for polarization distortion may include actively varying the polarization of the reference beam using polarization controller 240 and measuring the scattering coefficients at a number of different polarizations. Another method may include measuring the scattering coefficients while rapidly scrambling of the polarization state in one of the interferometer arms. This will produce an average value and will eliminate the polarization distortion. Other methods include adjustment of the modulation phase to produce a known and removable signal distortion. The polarization correction or compensation methods may be accomplished by polarization controller 240 under the control of control functions 297 (FIG. 2).

Time invariant noise (speckle pattern) may be caused by the coherent nature of the light source and may create a high frequency signal modulation. The spatial frequency of the speckle pattern may depend on a number of factors; one of which may be the acceptance angle of the receiving lens. Increasing the spatial frequency of the speckle pattern may allow its separation from the signal in the Fourier domain. Other methods may include signal processing methods such as zero mean technique zero average procedure, and other methods which may be used to substantially reduce the speckle pattern modulation of the received signal. All of these methods may be performed by the signal processing function 290. Alternatively, optical techniques may also be used.

It should be understood that the methods for correcting or compensating for tissue polarization effects and temporal and spatial-speckle pattern noise contributions may be performed separately or in combination.

On the scale of the typical focused optical interrogation beam, which may be about 0.1 mm, the tissue sample, especially in the case of human tissue, may not be homogeneous. Blood vessels, hair follicles, skin coloration etc. make repeatability of the optical measurement difficult to achieve. However, glucose concentration in the interstitial tissue is homogeneous and therefore it is possible to average the measurement over a tissue volume to eliminate tissue homogeneity effects without affecting the glucose measurement. In one embodiment a volumetric averaging technique may be used where the optical probe beam may be laterally translated to multiple locations and the results may be averaged. The beam may be translated using any suitable method or device, for example, by moving the probe using a mechanical device under control of receiver 235, or by adjusting optical element 315.

The system 200 may require calibration of two operational parameters: operating depth and calibration of the function $G_c$.

Operating depth: the sensitivity of glucose measurement is known to be a function of the depth of the probed layer from the skin surface. The optimal layer provides the highest response and thus best signal to noise. Because of motion artifacts and other time dependent changes, the optimal depth must be selected. The function of $m_s'(T)$ in tissue is also a function of z, the axial depth. The optimal interrogation depth (z) is where the greatest difference (corrected for optical distortions) occurs between $m_s'(T1)$ and $m_s'(T2)$. This point will also exhibit the highest sensitivity to changes in glucose concentration. Control functions 297 may include functions for self calibrating the operating depth. The functions may include automatically selecting T1 and T2 as well as measuring and comparing $m_s'(T1)$ and $m_s'(T2)$ over a range of tissue depths to determine which tissue depth yields the greatest different between $m_s'(T1)$ and $m_s'(T2)$.

Calibration of the function $G_c$ relative to glucose concentration: There are two ways to implement this calibration. The first one is comparing $G_c$ values to those measured in the blood. The second is to make use of the fact that the scattering centers have a constant refractive index and any variations in index mismatch are due to changes in the interstitial fluid. This means that in addition to glucose there is one other unknown, the refractive index of the interstitial fluid. Measuring scattering at one more temperature provides a way to form additional equations that can be used to the measure the refractive index of the interstitial fluid. In that case the complete calibration can be performed non-invasively with each measurement. Control functions 297 may be programmed to conduct an automated calibration of glucose concentration using one or both methods.

In summary, the disclosed embodiments provide a method and apparatus with the sensitivity and selectivity for effective non invasive blood glucose monitoring. Measurements are achieved that are independent of tissue parameters and therefore independent of changing physiological effects. The embodiments are capable of interrogating a specific, selectable tissue layer beneath the skin, and utilize thermal modulation to eliminate tissue-dependent interference from blood glucose determination.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims

What is claimed is:

1. A method of measuring glucose concentration in tissue comprising: measuring scattering coefficients of the tissue at each of a plurality of temperatures and at a selected tissue depth using optical coherence tomography; and determining the glucose concentration in interstitial fluid of the tissue as a function of the plurality of measured scattering coefficients, wherein said measured scattering coefficients are measured at each of said plurality of temperatures before physiological effects occur to said tissue.

2. The method of claim 1, further comprising automatically selecting a tissue depth at which to measure the scattering coefficients.

3. The method of claim 1, further comprising automatically performing a calibration of glucose concentration.

4. The method of claim 1, further comprising improving measurement accuracy of the glucose concentration by simultaneously reducing speckle noise and polarization distortion from the measured scattering coefficients and by performing volumetric averaging.

5. The method of claim 1, wherein the function of the measured scattering components includes separating the scattering coefficients into inactive components that do not change with glucose concentration and temperature and active components that do change with glucose concentration and temperature and utilizing the active components to determine the glucose concentration.

6. The method of claim 1, wherein the plurality of temperatures is applied to the tissue using a probe comprising: a thermoelectric cooler/heater; and a heat transfer device for rapid and uniform delivery of thermal energy across a surface of the tissue.

7. The method of claim 1, wherein said selected tissue depth comprises a depth at which highest sensitivity to changes in glucose concentration occurs.

8. The method of claim 1, wherein said scattering coefficients are measured at two temperatures and said glucose concentration is a function of the ratio of the measured scattering coefficient at one temperature to the measured scattering coefficient at a second temperature.

9. A system for measuring glucose concentration in tissue comprising: a probe for applying a plurality of temperatures to the tissue; and an instrument for measuring a scattering coefficient of light scattered by the tissue at each of the plurality of temperatures at a selected tissue depth using an optical coherence tomography system, and for determining the glucose concentration in interstitial fluid of the tissue as a function of the plurality of measured scattering coefficients, wherein said measured scattering coefficients are measured at each of said plurality of temperatures before physiological effects occur to said tissue.

10. The system of claim 9, wherein said instrument is further configured for automatically selecting a tissue depth at which to measure the scattering coefficients.

11. The system of claim 9, wherein said instrument is further configured for processing the function of the measured scattering coefficients to correct for non-constant intensity of a light beam used to measure the scattering coefficients.

12. The system of claim 9, wherein said instrument is further configured for processing the function of the measured scattering coefficients to compensate for birefringence of the tissue.

13. The system of claim 9, further comprising a polarization controller, wherein said instrument and the polarization controller are configured for correcting polarization distortion by measuring the scattering coefficients at a number of different polarizations of a reference beam used to measure the scattering coefficients.

14. The system of claim 9, further comprising a polarization controller, wherein said instrument and the polarization controller are configured for correcting for polarization effects by measuring the scattering coefficient while rapidly varying the polarization state in an interferometer arm of the optical coherence tomography system.

15. The system of claim 9, wherein said instrument is further configured for improving measurement accuracy of the glucose concentration by reducing speckle noise from the measured scattering coefficients.

16. The system of claim 9, wherein said instrument is further configured for improving measurement accuracy of the glucose concentration by performing volumetric averaging.

17. The system of claim 9, further comprising a polarization controller, wherein said instrument and the polarization controller are configured for improving measurement accuracy of the glucose concentration by simultaneously reducing speckle noise and polarization distortion and performing volumetric averaging.

18. The system of claim 9, wherein said instrument is further configured for performing an automatic calibration of glucose concentration.

19. The system of claim 9, wherein said instrument is further configured for determining the glucose concentration by separating the scattering coefficients into inactive components that do not change with glucose concentration and temperature and active components that do change with glucose concentration and temperature and utilizing the active components to determine the glucose concentration.

20. The system of claim 9, wherein the probe comprises: a thermoelectric cooler/heater; and a heat transfer device for rapid and uniform delivery of thermal energy across a surface of the tissue.

21. The system of claim 10, wherein said instrument selects a tissue depth at which highest sensitivity to changes in glucose concentration occurs.

22. The system of claim 9, wherein said instrument measures said scattering coefficients at two temperatures and said glucose concentration is determined based on the ratio of the measured scattering coefficient at one temperature to the measured scattering coefficient at a second temperature.

* * * * *